United States Patent
Lemoine et al.

(10) Patent No.: US 7,425,321 B2
(45) Date of Patent: Sep. 16, 2008

(54) ANHYDROUS ANTIPERSPIRANT STICK

(75) Inventors: Cyril Lemoine, Nogent sur Marne (FR); Véronique Douin, Paris (FR)

(73) Assignee: L'Oreal S.A., Paris (FR)

( * ) Notice: Subject to any disclaimer, the term of this patent is extended or adjusted under 35 U.S.C. 154(b) by 235 days.

(21) Appl. No.: 10/219,266

(22) Filed: Aug. 16, 2002

(65) Prior Publication Data

US 2003/0049219 A1 Mar. 13, 2003

(30) Foreign Application Priority Data

Aug. 17, 2001 (FR) .................................. 01 10903

(51) Int. Cl.
*A61Q 15/00* (2006.01)
*A61Q 19/00* (2006.01)
*A61K 8/02* (2006.01)

(52) U.S. Cl. .............................. 424/65; 424/66; 424/68; 424/400; 424/401

(58) Field of Classification Search .................. 424/65, 424/66, 68, 400, 401
See application file for complete search history.

(56) References Cited

U.S. PATENT DOCUMENTS

| | | | |
|---|---|---|---|
| 4,049,792 A | 9/1977 | Elsnau | |
| 4,126,679 A | 11/1978 | Davy et al. | |
| 4,524,062 A | 6/1985 | Laba et al. | |
| 5,102,656 A * | 4/1992 | Kasat | 424/66 |
| 5,302,381 A | 4/1994 | Greczyn et al. | |
| 5,376,363 A | 12/1994 | Benfatto et al. | |
| 5,378,452 A | 1/1995 | Greczyn et al. | |
| 5,916,546 A | 6/1999 | Sawin et al. | |
| 5,925,339 A | 7/1999 | Acuña et al. | |
| 6,126,928 A | 10/2000 | Swaile | |
| 6,177,066 B1 | 1/2001 | Pataut et al. | |

FOREIGN PATENT DOCUMENTS

| | | |
|---|---|---|
| CA | 1068215 | 12/1979 |
| DE | 24 49 880 A1 | 5/1975 |
| DE | 3120742 A1 | 3/1982 |
| EP | 0 135 315 A2 | 3/1985 |
| EP | 0 274 267 | 7/1988 |
| GB | 1 549 555 | 8/1979 |
| GB | 2 076 289 | 12/1981 |
| WO | WO 95/30405 | 11/1995 |
| WO | WO00/10521 | 3/2000 |
| WO | WO 00/74643 | 12/2000 |
| WO | WO 01/07007 | 2/2001 |
| WO | WO 01/13871 | 3/2001 |

OTHER PUBLICATIONS

CTFA Cosmetic Ingredient Handbook, First Edition, pp. 110-114.
REHEIS (A General Chemical Company), "Certificate of Analysis and Technical Data—Rezal 36 GP Superultrafine," Jan. 29, 2003 (2 pages).
REHEIS "Aluminum Zirconium Chlorohydrate Complexes" including Rezal 36 GP, (2 pages).
Reheis Inc. (Berkeley Heights, NJ), "Reach AZP-908 Superultrafine," Spec. No. BH-4600, Jun. 24, 2004 (1 page).
"Deodorant Stick," Cosmetics & Toiletries, vol. 105, p. 76 (Apr. 1990).
EPO Notice dated Jan. 10, 2007, including German document, "Henkel's Opposition Brief," dated Dec. 28, 2006, regarding European Patent EP 1 284 128 B1 (9 pages).

\* cited by examiner

*Primary Examiner*—Shelley A. Dodson
(74) *Attorney, Agent, or Firm*—Finnegan, Henderson, Farabow, Garrett & Dunner, LLP

(57) ABSTRACT

An anhydrous antiperspirant stick comprising: at least one antiperspirant active agent chosen from aluminium chlorohydrate and its complexes, such as complexes with zirconium; at least one solidifying agent chosen from natural waxes and synthetic waxes; and, at least one base chosen from inorganic and organic bases, such as anhydrous inorganic and organic bases. A method for reducing or eliminating the yellowing of anhydrous antiperspirant sticks based on waxes and on aluminium chlorohydrate or its complexes, by the inclusion therein of at least one base chosen from inorganic and organic bases.

31 Claims, No Drawings

ANHYDROUS ANTIPERSPIRANT STICK

The subject of the present invention is an anhydrous antiperspirant stick comprising, in one aspect of the invention: at least one antiperspirant active agent chosen from aluminium chlorohydrate and its complexes, such as complexes with zirconium; at least one solidifying agent chosen from waxes of natural and synthetic origin; and at least one base chosen from inorganic and organic bases, the at least one base, of course, either being anhydrous itself, meaning that the at least one base contains less than 5%, such as an amount less than 3%, and further an amount less than 0.5%, by weight of free or added water or otherwise present in an amount such that the antiperspirant stick nonetheless satisfies the definition of "anhydrous," as set forth hereinafter in paragraph [016].

Another aspect of the present invention relates to a method for reducing or eliminating the yellowing of anhydrous antiperspirant sticks based on at least one solidifying agent chosen from waxes of natural and synthetic origin and at least one antiperspirant active agent chosen from aluminium chlorohydrate and its complexes, such as complexes with zirconium, by including in the antiperspirant stick at least one base chosen from inorganic and organic bases.

Anhydrous antiperspirant sticks have been known and used for many years. They offer many advantages compared with other forms of presentation of antiperspirants such as sprays. These advantages are, for example, high safety during use and storage, the absence of propellant gases, which are harmful for the ozone layer, a simple and economical packaging, and good stability during storage due to the absence of drying phenomena.

In the cosmetic field, wax-based anhydrous sticks are well known in the field of deodorants and antiperspirants. In one embodiment of the present invention, anhydrous sticks based on waxes are free of ethanol, isopropanol, soap, and DBS (dibenzylidene sorbitol), i.e., none of these ingredients is included for any functional purpose in the anhydrous stick of the present invention.

Traditionally, a combination of two types of wax can be used, one having a relatively low melting point, for example, a melting point of less than 80° C., and the other having a high melting point, such as a melting point greater than 80° C.

The low melting point waxes are, for example, cetyl alcohol, myristyl alcohol, behenyl alcohol and the one most commonly described in the literature and used in commercial products is stearyl alcohol, which has a melting point of 60° C.

More recently, U.S. Pat. No. 6,177,066 B1 described anhydrous deodorant sticks comprising a mixture of waxes free of low melting point waxes, i.e., a mixture comprising waxes all having a melting point greater than 80° C. Solidification by such a combination of at least two high melting point waxes can produce a stick, which can last longer during use, and/or can lighten the skin less after application, while preserving good spreading properties such as unctuousness and slipperiness.

However, the inventors have observed that such anhydrous sticks based on waxes, which may require prolonged heating above 60° C. for their manufacture, and containing aluminium chlorohydrates as antiperspirant substance alone or present in complexes, such as complexes with zirconium, may be yellowish.

For antiperspirant sticks, the yellowish appearance is not a desirable criterion in terms of marketing.

Consumers seek instead white or transparent sticks.

Accordingly, the inventors, after numerous research studies carried out on the subject, have now discovered, unexpectedly and surprisingly, that by introducing an inorganic or organic base into an antiperspirant stick based on waxes and aluminium chlorohydrate or its complexes, their yellowing during manufacture could be avoided without adversely affecting the antiperspirant efficacy of resulting anhydrous antiperspirant sticks.

This is all the more surprising since it is in fact well known that, on neutralizing the aluminium salts, antiperspirant efficacy is lost.

In addition, in the antiperspirant sticks of the present invention, it has been possible to observe good resistance of the perfume to heat and over time.

One aspect of the present invention is thus an anhydrous antiperspirant stick comprising: at least one antiperspirant active agent chosen from aluminium chlorohydrate and its complexes; at least one solidifying agent chosen from waxes of natural origin and waxes of synthetic origin; and at least one base chosen from inorganic and organic bases, such as anhydrous bases.

Another aspect of the present invention is a method for reducing or eliminating the yellowing of an anhydrous antiperspirant stick, comprising including therein at least one base chosen from inorganic and organic bases, the stick further comprising at least one antiperspirant active agent chosen from aluminium chlorohydrate and its complexes, and at least one wax chosen from waxes of natural origin and waxes of synthetic origin.

According to the present invention, the expression "anhydrous," in the context of "anhyrdrous perspirant stick" is understood to mean that the composition of the stick contains less than 5%, such as an amount less than 3%, and further an amount less than 0.5%, by weight of free or added water, not counting the water of hydration associated with aluminium chlorohydrate, relative to the total weight of the composition.

Antiperspirant Active Agent

Representative aluminium chlorohydrates and their complexes which can be used in the antiperspirant sticks of the present invention, include the following substances used and approved by the F.D.A. (Food & Drug Administration): aluminium chlorohydrate, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, aluminium zirconium octachlorohydrate, aluminium zirconium octachlorohydrex GLY, aluminium zirconium pentachlorohydrate, aluminium zirconium pentachlorohydrex GLY, aluminium zirconium tetrachlorohydrate, aluminium zirconium trichlorohydrate, aluminium zirconium tetrachlorohydrex GLY, and aluminium zirconium trichlorohydrex-GLY, wherein the abbreviations PEG, PG and GLY denote polyethylene glycol, propylene glycol and glycine respectively. Commercial products of this type are sold, for example, by the company CLARIANT under the name LOCRON S (aluminium chlorohydrate), by the company REHEIS under the name REACH 301 or by the company GUILINI CHEMIE under the name ALOXICOLL PF 40 (aluminium chlorohydrex), by the company REHEIS under the name REZAL 67 SOLUTION (aluminium zirconium pentachlorohydrate sold as an aqueous solution containing 40% of active substance).

The "Active Substance" (on the basis of the total anhydrous aluminium salt excluding water of hydration and complexing agents) of said at least one antiperspirant active agent chosen from aluminium chlorohydrates and its complexes can be, for example, present in the sticks according to the present invention in an amount ranging from 1 to 50% by weight, such as an amount ranging from 1 to 30% by weight relative to the total weight of the composition.

Bases

Representative inorganic and organic bases used in the antiperspirant sticks of the present invention include (i) hydroxides of alkali and alkaline-earth metals and of ammonium, such as, for example, sodium hydroxide, potassium hydroxide, lithium hydroxide, calcium hydroxide, and magnesium hydroxide, (ii) sodium, calcium and zinc carbonates, (iii) urea, (iv) amino acids such as glycine, alanine, taurine, serine, arginine, valine, leucine, proline and the like, and their salts such as zinc glycinate, (v) organic amines such as ($C_1$-$C_{20}$)alkylamines and hydroxylamines such as, for example, triethylamine.

In one embodiment, the inorganic base is chosen from calcium hydroxide and calcium carbonate.

The said at least one base is present in the sticks according to the present invention in an amount, for example, ranging from 0.01 to 20% by weight, such as an amount ranging from 0.1 to 10% by weight relative to the total weight of the composition.

Solidifying Agent

The waxes of natural and synthetic origin and mixtures thereof which are used in the sticks of the present invention can perform such functions as to confer consistency on them, strengthen their structure, and confer on them the stiffness necessary to avoid their disintegration. Representative waxes include mixtures of polyethylenic synthetic waxes having a melting point of greater than 80° C., and of waxes of natural origin having a melting point of greater than 80° C., as is described in U.S. Pat. No. 6,177,066 B1.

In one embodiment, traditional solidifying systems can be used with one or more waxes, either of natural origin, or of synthetic origin having melting points, which may be less than 80° C. Thus, for example, it is possible to use fatty alcohols having from 8 to 40 carbon atoms, ethoxylated C12-C22 fatty alcohols containing from 2 to about 30 mol of ethylene oxide, esters and amides of fatty acids and of monohydroxy and polyhydroxy fatty acids having from 10 to 40 carbon atoms, and triglycerides, all these compounds being solid at 25° C., silicone wax, beeswax, paraffin wax and isoparaffin wax. Examples of such systems are described in patent applications WO-01/13871 pages 9-10, WO-01/07007 page 29 or WO-00/74643 pages 26-29, the disclosures of which are incorporated by reference herein.

The high melting point (>80° C.) polyethylene wax may be, for example, chosen from homopolymers of ethylene and copolymers of ethylene and of another copolymerizable monomer corresponding to the following formula (I):

$$CH_2=CHR \qquad (I)$$

in which R can be chosen from linear and branched alkyl chains optionally interrupted by at least one unit chosen from mono- and polyoxyalkylenated units, aryl and aralkyl radicals, —$CH_2COOH$, and —$CH_2CH_2OH$.

Exemplary alkyl radicals may include methyl, ethyl, propyl, isopropyl, decyl, dodecyl and octadecyl radicals.

The mono- and polyoxyalkylenated units can include, for example, mono- and polyoxyethylene groups and mono- and polyoxypropylene groups.

The aryl radical can be, for example, chosen from phenyl and tolyl radicals.

The aralkyl radical can be, for example, chosen from benzyl and phenethyl radicals.

In one embodiment, the average molecular weight of the high melting point polyethylene wax ranges, for example, from 400 to 1,000. In another embodiment, the average molecular weight of the high melting point polyethylene wax ranges from 400 to 700, such as an average molecular weight of 500.

In one embodiment, the polyethylene wax is chosen from homopolymers of ethylene, copolymers of ethylene and of propylene, copolymers of ethylene and of a monomer chosen from maleic anhydride and maleic acid, and oxidized and ethoxylated polyethylenes.

Representative homopolymers of ethylene include those marketed under the names POLYWAX 500, POLYWAX 655 and POLYWAX 1000 by the company PETROLITE.

Representative copolymers of ethylene include the copolymers of ethylene and of propylene marketed under the names PETROLITE® by the company PETROLITE, the copolymers of ethylene and of maleic anhydride marketed under the names CERAMER® by the company PETROLITE, the oxidized polyethylenes marketed under the names UNILIN® and UNICID® by the company PETROLITE, and the ethoxylated polyethylenes marketed under the names UNITHOX® by the company PETROLITE.

In one embodiment, the polyethylene wax is an ethylene homopolymer wax.

In one embodiment, the natural high melting point (>80° C.) wax is chosen from: waxes chosen from mineral, fossil, animal, and plant waxes, hydrogenated oils; fatty esters; fatty alcohols and polyalkoxylate fatty alcohols which are solid at 25° C.

Representative waxes of natural origin include microcrystalline waxes, ceresin, ozokerite, candelilla wax, carnauba wax, hydrogenated castor oil, hydrogenated palm oil, and hydrogenated copra oil.

In one embodiment, the natural wax is a high melting point ozokerite. Ozokerite is a fossil hydrocarbon having a complex composition corresponding to the solid residue from the evaporation of paraffin-rich petroleum.

A commercial ozokerite is, for example, the product CEROZO BLANCHE E 626®, which is a mixture of $C_{20-50}$ hydrocarbons which is marketed by the company BARLOCHER.

In one embodiment, the wax is a mixture of 5 to 20% by weight of synthetic polyethylene wax and 2 to 20% by weight of natural high melting point wax (>80° C.).

In one embodiment, the amount of polyethylene wax is greater than that of the natural wax. In another embodiment, the weight ratio of polyethylene wax to natural wax (polyethylene wax/natural wax) ranges from 10/1 to 1/1, such as a weight ratio ranging from 7/1 to 3/1.

In one embodiment, the at least one solidifying agent is present in the stick in an amount, for example, ranging from 1 to 50% by weight, such as an amount ranging from 5 to 30% by weight relative to the total weight of the composition.

The anhydrous antiperspirant stick of the invention may comprise, in addition, at least one emollient which can contribute to a smooth, dry and non-sticky sensation upon application of the stick to the skin.

The at least one emollient may be chosen from products such as volatile silicones, nonvolatile silicones and other nonvolatile emollients.

Volatile silicones are defined in a known manner as compounds which are volatile at room temperature. Representative volatile silicones include cyclic and linear volatile silicones of the dimethylsiloxane type in which the chains comprise from 3 to 9 silicone-containing residues. Other exemplary volatile silicones include cyclomethicones such as cyclotetrasiloxane and cyclopentasiloxane (D4 or D5).

Nonvolatile silicones are defined in a known manner as compounds having a low vapor pressure at room temperature. Representative nonvolatile silicones include: polyalkylsiloxanes, for example, linear polyalkylsiloxanes such as linear polydimethylsiloxanes and dimethicones marketed by the company Dow Corning under the name "Dow Corning 200 Fluid"; polyalkylarylsiloxanes such as polymethylphenylsiloxanes, marketed by the company Dow Corning under the name "Dow Corning 556 Fluid"; polyether and siloxane copolymers such as dimethicone copolyols.

Representative nonvolatile emollients include isoparaffins such as polydecenes, esters of $C_3$-$C_{18}$ alcohols with $C_3$-$C_{18}$ acids, such as glycerol monostearate, polyethylene glycol monostearate, isopropyl myristate, isopropyl adipate, isopropyl palmitate, octyl palmitate, esters of benzoic acid with $C_{12}$-$C_{18}$ alcohols and mixtures thereof, such as benzoates of $C_{12}$-$C_{15}$ fatty alcohols (Finsolv TN from FINETEX), $C_2$-$C_6$ polyols such as those chosen from glycerol, propylene glycol, and sorbitol, and polyalkylene glycol. Other exemplary nonvolatile emollients include polypropylene glycol (14) butyl ether, polyoxypropylenated myristyl alcohol containing 3 mol of propylene oxide (WITCONOL APM from WITCO), and triglycerides of $C_6$-$C_{18}$ fatty acids such as triglycerides of caprylic/capric acid.

In one embodiment the nonvolatile emollients are chosen form polydecenes, polypropylene glycol (14) butyl ether and isopropyl myristate.

In one embodiment, the at least one emollient can be present, for example, in the stick according to the present invention in an amount ranging from 10 to 70% by weight relative to the total weight of the composition.

The anhydrous antiperspirant stick of the invention may comprise, in addition, other adjuvants, for example, fillers such as talc and silica, demulcents, structuring agents such as PEG-8 distearate, antioxidants, opacifiers, stabilizers, moisturizing agents, vitamins, perfumes, preservatives, and any other ingredient customarily used in cosmetics for this type of application.

Of course persons skilled in the art would be careful to choose this or these optional additional compounds such that the advantageous properties intrinsically attached to the antiperspirant stick in accordance with the invention are not, or not substantially, impaired by the addition(s) envisaged.

Concrete examples, but which are not at all limiting, illustrating the invention will now be given.

EXAMPLES 1 to 3 AND COMPARATIVE EXAMPLE

The anhydrous antiperspirant sticks of the following composition were prepared:

|  | Example 1 | Example 2 | Example 3 | Comparative example |
|---|---|---|---|---|
| Wax: ozokerite | 2.75 | 2.75 | 2.75 | 2.75 |
| Wax: polyethylene (Polywax 500 from PETROLITE) | 12.00 | 12.00 | 12.00 | 12.00 |
| Cyclopentasiloxane | 18.90 | 18.95 | 17.40 | 19.40 |
| Polydecene | 15.50 | 15.75 | 14.00 | 16.00 |
| Isopropyl myristate | 15.00 | 15.00 | 15.00 | 15.00 |
| PPG-14 butyl ether | 10.00 | 10.00 | 10.00 | 10.00 |
| PEG-8 distearate | 2.50 | 2.50 | 2.50 | 2.50 |

-continued

|  | Example 1 | Example 2 | Example 3 | Comparative example |
|---|---|---|---|---|
| Antioxidant | 0.05 | 0.05 | 0.05 | 0.05 |
| Perfume | 1.30 | 1.30 | 1.30 | 1.30 |
| Base: calcium carbonate | 2.00 |  | 5.00 |  |
| Base: calcium hydroxide |  | 0.70 |  |  |
| Filler: talc |  | 1.00 |  | 1.00 |
| Aluminium Zirconium Tetrachlorohydrex Gly | 20.00 | 20.00 | 20.00 | 20.00 |
|  | 100.0 | 100.00 | 100.00 | 100.00 |

Contents Expressed in Grams

The waxes, emollients (polydecene, isopropyl myristate, PPG-14 butyl ether) and structuring agent (PEG-8 distearate), base, filler and preservative were mixed and heated to a temperature of about 60 to 90° C. and mixed until the waxes had melted and the mixture became homogeneous. The cyclopentasiloxane was then slowly added while maintaining the temperature between 60 and 90° C. Aluminium Zirconium Tetrachlorohydrex Gly was then added at the same temperature to the mixture, which was then cooled to around 65° C., and the perfume was added.

Colorimetric measurements were performed, on each of the sticks obtained, using the colorimeter MINOLTA CM2002 in the L*a*b* system.

In this system, the measurement of the parameter b*, designates the blue/yellow color axis, the higher the value of b*, the more yellow the shade.

A b* value of about 1.3 was obtained for the sticks of Examples 1, 2 and 3 according to the invention and a value of about 6.3 for the stick of the comparative example with no base and outside the invention.

Moreover, the sticks of Examples 1 to 3 according to the invention exhibited the same antiperspirant efficacy as that of the comparative example outside the invention.

EXAMPLE 4 AND COMPARATIVE EXAMPLE

The anhydrous antiperspirant sticks of the following composition were prepared:

Contents Expressed in Grams

|  | Example 4 | Comparative example |
|---|---|---|
| Stearyl alcohol | 14.00 | 14.00 |
| Hydrogenated castor oil | 4.00 | 4.00 |
| Talc | 3.20 | 3.20 |
| PEG-8 distearate | 1.00 | 1.00 |
| Calcium hydroxide | 2.00 |  |
| Cyclopentasiloxane | 50.80 | 52.80 |
| Perfume | 1.00 | 1.00 |
| Aluminium Zirconium Tetrachlorohydrex Gly | 24.00 | 24.00 |
|  | 100.00 | 100.00 |

The procedure was carried out as in the preceding examples, except that the melting temperature was 65 to 75° C.

The stick of Example 4 according to the invention gave a b* value lower than that of the comparative example outside the invention and its antiperspirant efficacy did not decrease relative to that of the comparative example.

What is claimed is:

1. An anhydrous antiperspirant stick comprising:
   at least one antiperspirant active agent chosen from aluminium chlorohydrate and its complexes;
   at least one solidifying agent which is a mixture of natural wax and polyethylene wax each having a melting point greater than 80° C.; and
   at least one base chosen from inorganic and organic bases, wherein the stick is free of ethanol, isopropanol, soap, and dibenzylidene sorbitol.

2. The stick according to claim 1, wherein the at least one antiperspirant active agent is chosen from aluminium chlorohydrate and its complexes with zirconium.

3. The stick according to claim 1, wherein the at least one base is chosen from inorganic bases.

4. The stick according to claim 3, wherein the at least one base is chosen from calcium hydroxide and calcium carbonate.

5. The stick according to claim 1, wherein the natural wax is chosen from mineral waxes, fossil waxes, animal waxes, plant waxes, hydrogenated oils, fatty esters, fatty alcohols, and polyalkoxylated fatty alcohols which are solid at 25° C.

6. The stick according to claim 5, wherein the natural wax is chosen from microcrystalline wax, ceresin wax, ozokerite wax, candelilla wax, carnauba wax, hydrogenated castor oil, hydrogenated palm oil, hydrogenated copra oil, triglycerides, beeswax, paraffin, and isoparaffin.

7. The stick according to claim 1, wherein the polyethylene wax is a homopolymer of ethylene having an average molecular weight of 500.

8. The stick according to claim 1, wherein a weight ratio between the polyethylene wax and the natural wax ranges from 10/1 to 1/1.

9. The stick according to claim 8, wherein the weight ratio between the polyethylene wax and the natural wax ranges from 7/1 to 3/1.

10. The stick according to claim 1, wherein the Active Substance of the at least one antiperspirant active agent, based on the total aluminium salt, excluding water of hydration and complexing agents, is present in an amount ranging from 1 to 50% by weight relative to the total weight of the composition.

11. The stick according to claim 10, wherein the Active Substance is present in an amount ranging from 1 to 30% by weight relative to the total weight of the composition.

12. The stick according to claim 1, wherein the at least one base is present in an amount ranging from 0.01 to 20% by weight relative to the total weight of the composition.

13. The stick according to claim 12, wherein the at least one base is present in an amount ranging from 0.1 to 10% by weight relative to the total weight of the composition.

14. The stick according to claim 1, wherein the at least one solidifying agent is present in an amount ranging from 1 to 50% by weight relative to the total weight of the composition.

15. The stick according to claim 14, wherein the at least one solidifying agent is present in an amount ranging from 5 to 30% by weight relative to the total weight of the composition.

16. The stick according to claim 1, further comprising at least one emollient.

17. The stick according to claim 16, wherein the at least one emollient is chosen from volatile silicones, polydecenes, polypropylene glycol (14) butyl ether, and isopropyl myristate.

18. The stick according to claim 16, wherein the at least one emollient is present in an amount ranging from 10 to 70% by weight relative to the total weight of the composition.

19. The stick according to claim 1, further comprising at least one ingredient chosen from fillers and other adjuvants.

20. The stick according to claim 1, wherein the at least one base is chosen from anhydrous inorganic and anhydrous organic bases.

21. A method for reducing or eliminating the yellowing of an anhydrous antiperspirant stick, the method comprising:
   including at least one base chosen from inorganic and organic bases to the antiperspirant stick, the stick otherwise comprising:
   at least one antiperspirant active agent chosen from aluminium chlorohydrate and its complexes; and
   at least one wax which is a mixture of natural wax and polyethylene wax each having a melting point greater than 80° C.

22. An anhydrous antiperspirant stick comprising:
   at least one antiperspirant active agent chosen from aluminium chlorohydrate and its complexes;
   at least one solidifying agent chosen from waxes of natural origin and waxes of synthetic origin; and
   at least one base which is calcium hydroxide,
   wherein the stick is free of ethanol, isopropanol, soap, and dibenzylidene sorbitol.

23. The stick according to claim 22, wherein the at least one antiperspirant active agent is chosen from aluminium chlorohydrate and its complexes with zirconium.

24. The stick according to claim 22, wherein the waxes of natural origin are chosen from microcrystalline wax, ceresin wax, ozokerite wax, candelilla wax, carnauba wax, hydrogenated castor oil, hydrogenated palm oil, hydrogenated copra oil, triglycerides, beeswax, paraffin, and isoparaffin.

25. The stick according to claim 22, wherein the waxes of synthetic origin are chosen from polyethylene waxes and silicone waxes.

26. The stick according to claim 22, wherein the Active Substance of the at least one antiperspirant active agent, based on the total aluminium salt, excluding water of hydration and complexing agents, is present in an amount ranging from 1 to 50% by weight relative to the total weight of the composition.

27. The stick according to claim 22, wherein calcium hydroxide is present in an amount ranging from 0.01 to 20% by weight relative to the total weight of the composition.

28. The stick according to claim 22, wherein the at least one solidifying agent is present in an amount ranging from 5 to 30% by weight relative to the total weight of the composition.

29. The stick according to claim 22, further comprising at least one emollient present in an amount ranging from 10 to 70% by weight relative to the total weight of the composition.

30. The stick according to claim 22, further comprising at least one ingredient chosen from fillers and other adjuvants.

31. A method for reducing or eliminating the yellowing of an anhydrous antiperspirant stick, the method comprising:
   including calcium hydroxide in the antiperspirant stick, the stick otherwise comprising:
   at least one antiperspirant active agent chosen from aluminium chlorohydrate and its complexes; and
   at least one solidifying agent chosen from waxes of natural origin and waxes of synthetic origin.

* * * * *